United States Patent
Usayapant et al.

(10) Patent No.: US 11,135,190 B2
(45) Date of Patent: *Oct. 5, 2021

(54) LEVOTHYROXINE LIQUID FORMULATIONS

(71) Applicant: Fresenius Kabi USA, LLC, Lake Zurich, IL (US)

(72) Inventors: Arunya Usayapant, Mundelein, IL (US); Basma M. Ibrahim, Lincolnshire, IL (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/511,220

(22) Filed: Jul. 15, 2019

(65) Prior Publication Data

US 2019/0336463 A1 Nov. 7, 2019

Related U.S. Application Data

(63) Continuation of application No. 15/700,258, filed on Sep. 11, 2017, now Pat. No. 10,398,669, which is a continuation of application No. 15/366,864, filed on Dec. 1, 2016, now Pat. No. 9,782,376.

(51) Int. Cl.
| | |
|---|---|
| *A61K 31/198* | (2006.01) |
| *A61K 9/08* | (2006.01) |
| *A61K 47/18* | (2017.01) |
| *A61K 47/02* | (2006.01) |
| *A61K 9/00* | (2006.01) |
| *A61K 33/18* | (2006.01) |

(52) U.S. Cl.
CPC .......... *A61K 31/198* (2013.01); *A61K 9/0019* (2013.01); *A61K 9/08* (2013.01); *A61K 33/18* (2013.01); *A61K 47/02* (2013.01); *A61K 47/18* (2013.01)

(58) Field of Classification Search
CPC .................................................... A61K 31/33
See application file for complete search history.

(56) References Cited

U.S. PATENT DOCUMENTS

| | | |
|---|---|---|
| 3,035,974 A | 5/1962 | Israel |
| 5,951,989 A | 9/1999 | Heymann |
| 6,383,471 B1 | 5/2002 | Chen et al. |
| 6,458,842 B1 | 10/2002 | Dickinson et al. |
| 6,645,526 B2 | 11/2003 | Hanshew, Jr. et al. |
| 6,706,255 B2 | 3/2004 | Dickinson et al. |
| 6,936,274 B2 | 8/2005 | Hanshew, Jr. et al. |
| 7,052,717 B2 | 5/2006 | Hanshew, Jr. et al. |
| 7,195,779 B2 | 3/2007 | Hanshew, Jr. et al. |
| 7,723,390 B2 | 5/2010 | Garavani et al. |
| 7,858,663 B1 | 12/2010 | Bristol et al. |
| 8,318,712 B2 | 11/2012 | Pierres et al. |
| 8,759,572 B2 | 6/2014 | Viscardi et al. |
| 8,779,000 B1 | 7/2014 | Parikh et al. |
| 9,006,289 B2 | 4/2015 | Jiang et al. |
| 9,050,307 B2 | 6/2015 | Psarrakis et al. |
| 9,168,238 B2 | 10/2015 | Jiang et al. |
| 9,168,239 B2 | 10/2015 | Jiang et al. |
| 9,345,772 B1 | 5/2016 | Parikh et al. |
| 9,428,444 B2 | 8/2016 | Rao et al. |
| 9,782,376 B1 | 10/2017 | Usayapant et al. |
| 2005/0059574 A1 | 3/2005 | Klein et al. |
| 2009/0270507 A1 | 10/2009 | Pierres et al. |
| 2016/0331711 A1 | 11/2016 | Parikh et al. |
| 2017/0319526 A1 | 11/2017 | Tengler |
| 2018/0064669 A1 | 3/2018 | Tengler |
| 2018/0153838 A1 | 6/2018 | Usayapant et al. |
| 2018/0214374 A1 | 8/2018 | Chandrashekhar et al. |
| 2019/0060217 A1 | 2/2019 | Chandrashekhar et al. |

FOREIGN PATENT DOCUMENTS

| | | |
|---|---|---|
| WO | 2015/151013 A1 | 10/2015 |
| WO | 2017/013591 A1 | 1/2017 |
| WO | 2017/077476 A1 | 5/2017 |
| WO | 2019/023791 A1 | 2/2019 |
| WO | 2019/094292 A1 | 5/2019 |

OTHER PUBLICATIONS

U.S. Appl. No. 15/366,864, filed Dec. 1, 2016.
U.S. Appl. No. 15/700,258, filed Sep. 11, 2017.
Bernareggi et al., "Oral Liquid Formulation of Levothyroxine is Stable in Breakfast Beverages and May Improve Thyroid Patient Compliance," *Pharmaceutics*, 5: 621-633 (2013).
Collier et al., "Influence of Formulation and Processing Factors on Stability of Levothyroxine Sodium Pentahydrate," *AAPS PharmSciTech*, 11(2): 818-825 (2010).
Kannamkumarath et al., "Determination of Levothyroxine and its Degradation Products in Pharmaceutical Tablets by HPLC-UV-ICP-MS," *J. Anal. At. Spectrom.*, 19: 107-113 (2004).
Kazemifard et al., "Identification and Quantitation of Sodium-Thyroxine and its Degradation Products by LC Using Electrochemical and MS Detection," *J. Pharm. Biomed. Anal.*, 25: 697-711 (2001).
Patel, "The Effect of Formulation and Processing Variables on the Stability of Levothyroxine Sodium Tablets," Dissertation submitted to Univ. Cincinnati Coll. of Pharmacy: pp. 1-151 (May 2003).
Patel et al., "The Effect of Excipients on the Stability of Levothyroxine Sodium Pentahydrate Tablets," *Int. J. Pharm.*, 264: 35-43 (2003).
*Remington Pharmaceutical Science, 17th Edition*, Alfonso R. Gennaro, Editor, Mack Publishing Company, Easton, PA, USA, pp. 836-837, 1455-1472 (1985).
Schering Corp., Prescribing Information for LEVENTA Levothyroxine Sodium Solution: pp. 1-5 (Oct. 2010).

(Continued)

*Primary Examiner* — San Ming R Hui
(74) *Attorney, Agent, or Firm* — Leydig, Voit & Mayer, Ltd.

(57) ABSTRACT

The present invention is directed to a pharmaceutical product which includes a liquid formulation comprising levothyroxine or a pharmaceutically acceptable salt thereof. The formulation of the present invention includes tromethamine, sodium iodide, and water and has a pH of about 9.0 to about 11.5. The liquid formulation according to the invention is stable and ready-to-use.

16 Claims, No Drawings

(56) References Cited

OTHER PUBLICATIONS

Shah et al., "Stability Indication Validated HPLC Method for Quantification of Levothyroxine with Eight Degradation Peaks in the Presence of Excipients," *Int. J. Pharm.*, 360: 77-82 (2008).
Stadalman et al., "Stability of Levothyroxine Sodium 0.4 µg/mL in 0.9% Sodium Chloride Injection," *Prog. Transplant.*, 19(4): 354-356 (2009).
Strong et al., "Stability of Levothyroxine in Sodium Chloride for IV Administration," *Can. J. Hosp. Pharm.*, 63(6): 437-443 (2010).
United States Pharmacopeial Convention, "Levothyroxine Sodium," United States Pharmacopeia and National Formulary (Revision Bulletin): pp. 1-3 (Oct. 2010).
Won, "Kinetics and Degradation of Levothyroxine in Aqueous Solution and in Solid State," *Pharm. Res.*, 9(1): 131-137 (1992).
Pramanick et al., "Excipient Selection in Parenteral Formulation Development," *Pharma Times* 45(3): 65-77 (2013).
European Patent Office, International Search Report in International Application No. PCT/US2017/062019 (dated Feb. 21, 2018).
European Patent Office, Written Opinion in International Application No. PCT/US2017/062019 (dated Feb. 21, 2018).

LEVOTHYROXINE LIQUID FORMULATIONS

CROSS-REFERENCE TO RELATED APPLICATIONS

This patent application is a continuation of U.S. patent application Ser. No. 15/700,258, filed Sep. 11, 2017, now U.S. Pat. No. 10,398,669, which is a continuation of U.S. patent application Ser. No. 15/366,864, filed Dec. 1, 2016, now U.S. Pat. No. 9,782,376, the disclosures of which are incorporated herein by reference in their entireties for all purposes.

BACKGROUND OF THE INVENTION

Levothyroxine sodium for injection is a sterile lyophilized product for parenteral administration of levothyroxine sodium for thyroid replacement therapy. Levothyroxine sodium for injection is particularly useful when thyroid replacement is needed on an urgent basis, for short term thyroid replacement, and/or when oral administration is not possible, such as for a patient in a state of myxedema coma.

Full chemical names for levothyroxine sodium include 4-(4-hydroxy-3,5-diiodophenoxy)-3,5-diiodo-L-phenylalanine sodium, and L-tyrosine-O-(4-hydroxy-3,5-diiodophenyl)-3,5-diiodo-monosodium salt. Levothyroxine sodium has a molecular weight of approximately 798.85 and the following chemical structure:

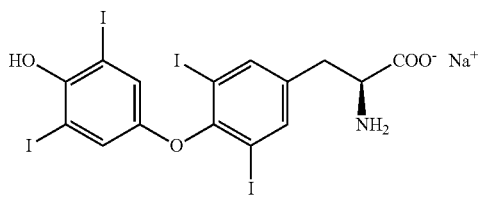

Conventional formulations of levothyroxine sodium for injection are preservative-free lyophilized powders containing levothyroxine sodium and the excipients mannitol, sodium phosphate buffer, and sodium hydroxide. Administration of the conventional formulations involve reconstitution of the lyophilized powder in 0.9% sodium chloride injection (USP) to provide an injectable solution.

However, use of the conventional lyophilized formulations requires reconstitution or dilution by healthcare practitioners prior to use. Once reconstituted, the levothyroxine sodium solutions have a limited stability, and must be used within a few hours of reconstitution. In addition, contaminants may be introduced into the solutions during the reconstitution process, thereby compromising patient safety.

It has been shown that levothyroxine in oral tablets and in aqueous solutions undergoes degradation. Major degradation products of levothyroxine are known to include 3,3',5-triiodothyronine (T3) 3,5-diiodothyronine (T2) 3,3',5,5'-tetraiodothyroacetic acid (TTAA4) 3,3',5-triiodothyroacetic acid (TTAA3) and 3,5-diiodothyroacetic acid (TTAA2) (Kannamkumarath et al., *J. Anal. At. Spectrom.*, 2004, 19: 107-113 and Patel et al., *Int. J. Pharm.*, 2003, 264: 35-43)). 3,3',5-triiodothyronine, known as liothyronine or T3, is a major degradant. Aqueous solutions of levothyroxine sodium have been shown to be more stable at basic pH than at acidic pH, but significant degradation of levothyroxine sodium also has been shown to occur at basic pH (Patel et al., *Int. J. Pharm.*, 2003, 264: 35-43).

Thus, there remains a need in the art for a ready-to-use injectable formulation of levothyroxine sodium that exhibits storage stability.

BRIEF SUMMARY OF THE INVENTION

The invention provides a liquid formulation comprising levothyroxine or a pharmaceutically acceptable salt thereof, tromethamine, sodium iodide, and water, wherein the formulation has a pH of about 9.0 to about 11.5.

The invention also provides a liquid formulation comprising (a) levothyroxine or a pharmaceutically acceptable salt thereof in a concentration of about 20 mcg/mL to about 100 mcg/mL, (b) tromethamine in a concentration of about 5 mg/mL to about 20 mg/mL, (c) sodium iodide in a concentration of about 100 mcg/mL to about 300 mcg/mL, (d) sodium chloride, and (e) water, wherein the formulation has a pH of about 9.8 to about 10.8.

DETAILED DESCRIPTION OF THE INVENTION

The invention provides a liquid formulation comprising levothyroxine or a pharmaceutically acceptable salt thereof, tromethamine, sodium iodide, and water, wherein the formulation has a pH of about 9.0 to about 11.5. The liquid formulation according to the invention is stable and ready-to-use.

As used herein, a "ready-to-use" formulation is a sterile, injectable formulation that is not reconstituted from a solid by a healthcare provider prior to use. Rather, a ready-to-use formulation is supplied by a pharmaceutical manufacturer in a suitable container (e.g., vial, syringe, bag, container) in liquid form. In some embodiments, a ready-to-use formulation is an injectable formulation that is administered to a subject without dilution. In other embodiments, a ready-to-use formulation is a concentrated, liquid solution that must be diluted prior to administration to a subject. Thus, in some embodiments, the formulation of the present invention can be further diluted in an appropriate diluent such as, for example, WFI (water for injection), 0.9% sodium chloride, or 5% dextrose to a lower levothyroxine concentration.

The formulation according to the present invention is stable. As used herein, the terms "stable" and "stability" encompass any characteristic of the formulation which may be affected by storage conditions including, without limitation, potency, total impurities, levothyroxine degradation products, specific optical rotation, optical purity, water content, appearance, viscosity, sterility, and color and clarity. The storage conditions which may affect stability include, for example, duration of storage, temperature, humidity, and/or light exposure.

In certain embodiments, a stable levothyroxine formulation refers to a formulation that retains at least about 90%, or about least about 95%, or at least about 96%, or at least about 98%, of the labeled concentration of levothyroxine or pharmaceutically acceptable salt thereof after storage under typical and/or accelerated conditions. In further embodiments, a stable levothyroxine formulation refers to less than about 15% (area percent), or less than about 10% (area percent), or less than about 7% (area percent), or less than about 5% (area percent), or less than about 2% (area percent) of levothyroxine-related impurities are present after storage under typical and/or accelerated conditions.

In some embodiments, the liquid formulation of the invention is stable for at least 12 months, at least 18 months, at least 24 months, or at least 36 months at refrigerated temperature (e.g., at 5±2° C.). In other embodiments, the liquid formulation of the invention is stable for at least 12 months, at least 18 months, at least 24 months, or at least 36 months at room temperature (e.g., at 25±2° C.).

Methods for determining the stability of a formulation of the invention with respect to a given parameter are well-known to those of skill in the art. For example, individual impurities and total impurities can be assessed by high-performance liquid chromatography (HPLC) or thin layer chromatography (TLC). Unless otherwise indicated to the contrary, a percentage amount of liothyronine, other individual impurities, or total impurities reported herein in the formulation is determined by a peak area percent method using HPLC.

The formulation comprises levothyroxine or any pharmaceutically acceptable salt thereof. Preferably, the formulation comprises levothyroxine sodium. In an embodiment, the levothyroxine sodium is levothyroxine sodium pentahydrate, which is the sodium salt of the levo-isomer of thyroxine, an active physiological substance found in the thyroid gland.

When the formulation comprises levothyroxine sodium, the levothyroxine sodium can be present in the formulation in any suitable concentration. Typically, levothyroxine sodium can be present in the formulation at a concentration of about 5 mcg/mL (micrograms/milliliter) or more, for example, about 10 mcg/mL or more, about 15 mcg/mL or more, about 20 mcg/mL or more, about 25 mcg/mL or more, about 30 mcg/mL or more, about 35 mcg/mL or more, about 40 mcg/mL or more, or about 45 mcg/mL or more.

Alternatively, levothyroxine sodium can be present in the formulation at a concentration of about 500 mcg/mL or less, for example, about 450 mcg/mL or less, about 400 mcg/mL or less, about 350 mcg/mL or less, about 300 mcg/mL or less, about 250 mcg/mL or less, about 200 mcg/mL or less, or about 150 mcg/mL or less.

Levothyroxine sodium can be present in the formulation in a concentration bounded by any two of the aforementioned endpoints. For example, levothyroxine sodium can be present in the formulation in a concentration of about 5 mcg/mL to about 500 mcg/mL, for example, about 10 mcg/mL to about 450 mcg/mL, about 15 mcg/mL to about 400 mcg/mL, about 20 mcg/mL to about 350 mcg/mL, about 25 mcg/mL to about 300 mcg/mL, about 30 mcg/mL to about 300 mcg/mL, about 35 mcg/mL to about 300 mcg/mL, about 40 mcg/mL to about 300 mcg/mL, about 45 mcg/mL to about 300 mcg/mL, or about 50 mcg/mL to about 250 mcg/mL, or about 20 mcg/mL to about 100 mcg/mL.

In a preferred embodiment, levothyroxine sodium is present at a concentration of about 20 mcg/mL. In another preferred embodiment, levothyroxine sodium is present at a concentration of about 40 mcg/mL. In yet another preferred embodiment, levothyroxine sodium is present at a concentration of about 100 mcg/mL.

The formulation can be provided in any suitable volume. In some embodiments, the volume of the formulation is about 0.5 mL or more, e.g., about 1 mL or more, about 3 mL or more, about 5 mL or more, about 8 mL or more, about 10 mL or more, about 20 mL or more, or about 50 mL or more. In other embodiments, the volume of the formulation is about 200 mL or less, e.g., about 150 mL or less, about 100 mL or less, about 50 mL or less, about 30 mL or less, about 15 mL or less, about 10 mL or less, or about 5 mL or less. The formulation can be provided in a volume bounded by any two of the aforementioned endpoints. For example, the formulation can be provided in a volume of about 1 mL to about 200 mL, about 1 mL to about 50 mL, about 3 mL to about 30 mL, about 5 mL to about 100 mL, or about 3 mL to about 10 mL. In certain preferred embodiments, the volume of the formulation is about 5 mL. One of ordinary skill in the art can readily select an appropriate container based upon the volume of the formulation.

The formulation comprises at least one stabilizing agent. The stabilizing agent serves to stabilize levothyroxine or a pharmaceutically acceptable salt thereof in the liquid formulation.

In some embodiments, the stabilizing agent is an amine. Non-limiting examples of suitable amines include tromethamine (i.e., 2-amino-2-hydroxymethyl-propane-1,3-diol or Tris), bis(2-hydroxyethyl)-imino-tris(hydroxymethyl)methane (Bis-tris or Bis-tris methane), monoethanolamine, diethanolamine, triethanolamine, 2-amino-2-methyl-1,3-propanediol, 2-dimethylamino-2-methyl-1-propanediol, 2-amino-2-ethylpropanol, 2-amino-1-butanol, and 2-amino-2-methyl-1-propanol. Preferably, the amine is tromethamine.

The amine can be present in the formulation in any suitable concentration. Typically, the amine can be present in the formulation at a concentration of about 1 mg/mL (milligram/milliliter) or more, for example, about 5 mg/mL or more, about 10 mg/mL or more, about 15 mg/mL or more, or about 20 mg/mL or more. Alternatively, the amine can be present in the formulation at a concentration of about 50 mg/mL or less, for example, about 45 mg/mL or less, about 40 mg/mL or less, about 35 mg/mL or less, about 30 mg/mL or less, about 25 mg/mL or less, or about 20 mg/mL or less.

Thus, the amine can be present in the formulation in a concentration bounded by any two of the aforementioned endpoints. For example, the amine can be present in the formulation in a concentration of about 1 mg/mL to about 50 mg/mL, for example, about 1 mg/mL to about 50 mg/mL, about 5 mg/mL to about 45 mg/mL, about 5 mg/mL to about 40 mg/mL, about 5 mg/mL to about 35 mg/mL, about 5 mg/mL to about 30 mg/mL, about 5 mg/mL to about 25 mg/mL, or about 5 mg/mL to about 20 mg/mL. In a preferred embodiment, the amine is tromethamine present at a concentration of about 20 mg/mL. In another preferred embodiment, the amine is tromethamine present at a concentration of about 10 mg/mL.

In some embodiments, the stabilizing agent is a salt of iodine, such as sodium iodide or potassium iodide. In some embodiments, the formulation comprises sodium iodide at a concentration of about 10 mcg/mL or more, e.g., 25 mcg/mL or more, 50 mcg/mL or more, 75 mcg/mL or more, 100 mcg/mL or more, 125 mcg/mL or more, 150 mcg/mL or more, 175 mcg/mL or more, or 200 mcg/mL or more. In other embodiments, the formulation comprises sodium iodide at a concentration of about 500 mcg/mL or less, e.g., 450 mcg/mL or less, 400 mcg/mL or less, 350 mcg/mL or less, 300 mcg/mL or less, 250 mcg/mL or less, 200 mcg/mL or less, 175 mcg/mL or less, or 150 mcg/mL or less.

Thus, the sodium iodide can be present in the formulation in a concentration bounded by any two of the aforementioned endpoints. For example, the sodium iodide can be present in the formulation in a concentration of about 10 mcg/mL to about 500 mcg/mL, for example, about 50 mcg/mL to about 400 mcg/mL, about 100 mcg/mL to about 300 mcg/mL, about 125 mcg/mL to about 300 mcg/mL, about 125 mcg/mL to about 250 mcg/mL, about 125 mcg/mL to about 200 mcg/mL, about 125 mcg/mL to about 175 mcg/mL, or about 125 mcg/mL to about 150 mcg/mL. In a preferred embodiment, the sodium iodide is present at a concentration of about 140 mcg/mL.

The formulation can comprise one, two, or three or more stabilizing agents. In certain embodiments, the formulation comprises an amine and a salt of iodine, preferably tromethamine and sodium iodide. In some embodiments, the formulation comprises about 10 mg/mL tromethamine and about 140 mcg/mL sodium iodide.

The formulation comprises an isotonicity adjuster. Non-limiting examples of suitable isotonicity adjusters include sodium chloride, potassium chloride, dextrose, glycerin, and mannitol. In a preferred embodiment, the isotonicity adjuster is sodium chloride.

The isotonicity adjuster can be present at any suitable concentration. In some embodiments, the isotonicity adjuster is present at a concentration that renders the formulation isotonic or approximately isotonic with cells (e.g., red blood cells) and/or isotonic or approximately isotonic to blood plasma.

The formulation optionally comprises a pH adjuster. The pH adjuster can be any suitable pH adjuster, for example, the pH adjuster can be sodium hydroxide, potassium hydroxide, hydrochloric acid, or combinations thereof. In a preferred embodiment, the pH adjuster is sodium hydroxide, hydrochloric acid, or a combination thereof.

The formulation can have any suitable pH. Typically, the formulation can have a pH of about 9.0 or more including, for example, about 9.0 or more, about 9.2 or more, about 9.4 or more, about 9.6 or more, about 9.8 or more, about 10.0 or more, or about 10.2 or more. Alternatively, the formulation can have a pH of about 11.5 or less including, for example, about 11.3 or less, about 11.1 or less, about 11.0 or less, about 10.9 or less, about 10.8 or less, about 10.7 or less, about 10.6 or less, or about 10.5 or less.

The formulation can have a pH bounded by any two of the above endpoints recited for the formulation. For example the formulation can have a pH of about 9.0 to about 11.5 including, for example, about 9.0 to about 11.0, about 9.2 to about 10.8, about 9.2 to about 10.8, about 9.4 to about 10.8, about 9.6 to about 10.8, about 9.8 to about 10.8, about 10.0 to about 10.8, about 10.0 to about 10.7, about 10.0 to about 10.5, or about 10.2 to about 10.6.

Tromethamine has a buffering range of about 7 to about 9. In a preferred embodiment, the pH of the formulation is about 9.8 to about 10.8, which is above the buffering range of tromethamine. While not wishing to be bound by any particular theory, it is believed that tromethamine exerts a stabilizing effect on levothyroxine by a mechanism unrelated to buffering of the formulation.

In a preferred embodiment, the formulation comprises (a) levothyroxine or a pharmaceutically acceptable salt thereof in a concentration of about 20 mcg/mL to about 100 mcg/mL, (b) tromethamine in a concentration of about 5 mg/mL to about 20 mg/mL, (c) sodium iodide in a concentration of about 100 mcg/mL to about 300 mcg/mL, (d) sodium chloride, and (e) water, wherein the formulation has a pH of about 9.8 to about 10.8.

The formulation that comprises levothyroxine or a pharmaceutically acceptable salt thereof, tromethamine, sodium iodide, sodium chloride, and water may further include one or more other substances. Non-limiting examples of other substances include diluents, salts, buffers, stabilizers, solubilizers, and preservatives. In certain embodiments, the other substance is a cyclodextrin, such as hydroxypropyl-β-cyclodextrin or sulfobutylether β-cyclodextrin.

A formulation comprising levothyroxine or a pharmaceutically acceptable salt thereof, tromethamine, sodium iodide, sodium chloride, and water can be prepared by using any suitable technique, many of which are known to those skilled in the art. The formulation can be prepared in a batch or continuous process. Generally, the formulation can be prepared by combining the components thereof in any order. The term "component" as used herein includes individual ingredients (e.g., levothyroxine sodium, tromethamine, sodium iodide, sodium chloride, optional pH adjuster, etc.) as well as any combination of ingredients (e.g., levothyroxine sodium, tromethamine, sodium iodide, sodium chloride, optional pH adjuster, etc.). In some embodiments, the formulation is formed by combining the components together in a vessel. The components can be combined in any order.

In some embodiments, the water is added to a suitable vessel, then the tromethamine, sodium iodide, and sodium chloride are added, either sequentially or together, and the mixture is stirred. Next, the pH is adjusted to the desired value. Subsequently, the levothyroxine sodium is added, and the mixture is stirred until the levothyroxine sodium is dissolved. In some embodiments, the water and sodium chloride are combined and stirred until the sodium chloride is dissolved to provide an aqueous solution of sodium chloride. Subsequently, the levothyroxine sodium, tromethamine, and sodium iodide are added, either sequentially or together, and the mixture is stirred. Next, the pH is adjusted to the desired value. Optional ingredients, such as diluents, salts, buffers, stabilizers, solubilizers, and preservatives, can be provided to the formulation at any stage in its preparation.

In some embodiments, the formulation is filtered through one or more filters prior to filling the composition into one or more suitable containers, such as a vial, an ampoule, a cartridge, a syringe, or a bag. Preferably, one or more of the filtration steps and the filling step are performed under aseptic conditions in order to provide a sterile container comprising a sterile formulation. A sterile formulation of the invention is preferably one in which substantially all forms of microbial life have been destroyed by an appreciable amount to meet the sterilization criteria set forth in the U.S. Pharmacopeia. See U.S. Pharmacopeia 32, NF 27, 1 (2009) 80-86.

The invention also provides a container comprising a formulation comprising levothyroxine sodium, tromethamine, sodium iodide, sodium chloride, optional pH adjustor, and any other optional components. In certain embodiments, the container is a vial, an ampoule, a bag, a bottle, a cartridge, or a syringe. In some embodiments, the container, the composition, or both the container and the composition are sterile. Preferably, the container is sealed by way of a closure, such as a stopper, plunger, and/or tip-cap.

The container and closure can be made of glass, plastic, and/or rubber. One or more surfaces of the container and/or closure can be treated with a compound to limit reactivity with one or more components of the formulation. In some embodiments, the container and/or closure are treated with silicon. In other embodiments, the container is treated with ammonium sulfate (($NH_4)_2SO_4$). The container can be clear or opaque, and can be any color. In some embodiments, the container is flint colored. In other embodiments, the container is amber colored.

In certain embodiments, the invention provides a pre-filled syringe containing a formulation of the invention described herein. In certain embodiments, a syringe according to the invention is a component of an autoinjector.

In some embodiments, the liquid formulation of the invention contains not more than 1.5% liothyronine (T3). In other embodiments, the liquid formulation contains not more than 1.25% liothyronine, e.g., not more than 1.0% liothyronine, not more than 0.9% liothyronine, not more than 0.8% liothyronine, not more than 0.7% liothyronine, not more than 0.6% liothyronine, not more than 0.5% liothyronine, not more than 0.4% liothyronine, not more than 0.35% liothyronine, not more than 0.30% liothyronine, not more than 0.25% liothyronine, not more than 0.2% liothyronine, or any range therein. For example, in certain embodiments, the liquid formulation contains 0.2%-1.5% liothyronine, 0.25%-1.25% liothyronine, 0.25%-1.0% liothyronine, 0.3%-0.9% liothyronine, 0.2%-0.4% liothyronine, 0.25%-0.4% liothyronine, or 0.25%-0.35% liothyronine.

In some embodiments, the liquid formulation contains not more than a specified amount of liothyronine as measured after storage of the formulation at a predetermined temperature for a predetermined time period. In certain embodiments, the liquid formulation contains not more than 1.0% liothyronine, e.g., not more than 0.8% liothyronine, not more than 0.6% liothyronine, not more than 0.5% liothyronine, not more than 0.4% liothyronine, not more than 0.30% liothyronine, not more than 0.2% liothyronine, or any range therein as measured after storage of the formulation at 25±2° C. for a period of four months. In other embodiments, the liquid formulation contains not more than 1.5% liothyronine, e.g., not more than 1.25%, not more than 1.0%, not more than 0.8%, not more than 0.6%, not more than 0.5%, not more than 0.4%, or any range therein as measured after storage of the formulation at 40±2° C. for a period of four months.

In some embodiments, the liquid formulation of the invention contains not more than 5.0% total impurities. In other embodiments, the liquid formulation contains not more than 4.0% total impurities, e.g., not more than 3.5% total impurities, not more than 3.0% total impurities, not more than 2.5% total impurities, not more than 2.0% total impurities, not more than 1.5% total impurities, not more than 1.25% total impurities, not more than 1.0% total impurities, not more than 0.9% total impurities, not more than 0.8% total impurities, not more than 0.7% total impurities, or any range therein. For example, in certain embodiments, the liquid formulation contains 1.0%-5.0% total impurities, 1.5%-3.5% total impurities, 0.8%-3.0% total impurities, 0.7%-2.0% total impurities, 1.25%-4.0% total impurities, 0.8%-1.5% total impurities, or 0.9%-1.25% total impurities.

In some embodiments, the liquid formulation contains not more than a specified amount of total impurities as measured after storage of the formulation at a predetermined temperature for a predetermined time period. In certain embodiments, the liquid formulation contains not more than 2.0% total impurities, e.g., not more than 1.5% total impurities, not more than 1.25% total impurities, not more than 1.0% total impurities, not more than 0.9% total impurities, not more than 0.8% total impurities, not more than 0.7% total impurities, or any range therein as measured after storage of the formulation at 25±2° C. for a period of four months. In other embodiments, the liquid formulation contains not more than 5.0% total impurities, e.g., not more than 4.0% total impurities, not more than 3.5% total impurities, not more than 3.0% total impurities, not more than 2.5% total impurities, not more than 2.0% total impurities, not more than 1.5% total impurities, or any range therein as measured after storage of the formulation at 40±2° C. for a period of four months.

The invention also provides a method of stabilizing a levothyroxine formulation by forming a mixture comprising levothyroxine or a pharmaceutically acceptable salt thereof, tromethamine, sodium iodide, sodium chloride, and water, thereby stabilizing the formulation. The identity and amounts of levothyroxine or pharmaceutically acceptable salt thereof, tromethamine, sodium iodide, and sodium chloride present in the mixture as well as the pH can be the same as the identity and amounts of these components and the pH described herein with respect to a formulation of the invention. The formulation formed by the method of stabilizing a levothyroxine formulation can have the same stability characteristics as the stability characteristics described herein with respect to a formulation of the invention, particularly with regard to total impurities and liothyronine.

The formulation according to the invention is suitable for administration to a subject to treat or prevent a disease or condition. Preferably, the subject is a mammal. More preferably, the mammal is a human. Preferably, the disease or condition is a disease or condition that is treatable by the administration of levothyroxine or a pharmaceutically acceptable salt thereof, such as hypothyroidism. In some embodiments, the condition is myxedema coma.

The following examples further illustrate the invention but, of course, should not be construed as in any way limiting its scope.

Example 1

This example demonstrates the stability of exemplary formulations comprising levothyroxine sodium, tromethamine, and water as a function of the pH of the formulation.

Separate samples containing levothyroxine sodium at a concentration of 20 mcg/mL, tromethamine at a concentration of 10 mg/mL in normal saline (0.9% NaCl in water) were adjusted to various pH levels. One sample additionally contained hydroxypropyl (HP) β-cyclodextrin at a concentration of 10 mg/mL. 5 mL of each sample was filled into 10 cc amber tubing vials, and the vials were stoppered with 20 mm stoppers under nitrogen. The samples were stored at temperatures of 25° C., 40° C. and 55° C. The samples stored at 55° C. were analyzed by HPLC at 1 and 4 weeks (W) of storage. The samples stored at 40° C. were analyzed by HPLC at 4 W and 3 months (M) of storage. The samples stored at 25° C. were analyzed by HPLC at 3M of storage.

The HPLC conditions were as follows:
Column: Waters SYMMETRY™ C8 (5 μm, 4.6×150 mm) HPLC column
Mobile Phase A: Sodium heptanesulfonate/Acetonitrile/Water/Methanol/$H_3PO_4$ (4.023 g/800 mL/1600 mL/1600 mL/4 mL)
Mobile Phase B: Sodium heptanesulfonate/Acetonitrile/Water/Methanol/$H_3PO_4$ (2.013 g/1000 mL/100 mL/900 mL/2 mL)
Diluent: 0.01 N NaOH
Column temperature: 25° C.
Flow rate: 1.5 mL/min
Injection volume: 40-200 μL
Autosampler temperature: 5° C.
Detection: UV at 225 nm
Separation mode: Gradient
Gradient program:

| Time (minutes) | % Mobile Phase | |
|---|---|---|
| | A | B |
| 25 | 100 | 0 |
| 40 | 10 | 90 |

-continued

| Time (minutes) | % Mobile Phase A | % Mobile Phase B |
|---|---|---|
| 50 | 10 | 90 |
| 51 | 100 | 0 |
| 60 | 100 | 0 |

The relative response time (RRT) for liothyronine to levothyroxine was approximately 0.73.

The results for liothyronine, largest unknown impurity, and total impurities as determined by peak area percent are set forth in Table 1.

TABLE 1

| | | | | | | |
|---|---|---|---|---|---|---|
| Levothyroxine Na (mcg/mL) | | | 20 | | | |
| Tromethamine (mg/mL) | | | 10 | | | |
| HP-β-cyclodextrin (mg/mL) | | — | — | — | — | 10 |
| Solvent | | | | Normal saline | | |
| pH | | 8 | 9 | 9.5 | 10 | 9 |
| 55° C., 1 W | % Liothyronine | 15.2 | 2.7 | 1.2 | 0.6 | 2.7 |
| | % largest unknown impurity | 1.59 | 0.67 | 0.50 | 0.27 | 0.86 |
| | % total impurities | 17.5 | 3.6 | 2.2 | 1.5 | 4.0 |
| 55° C., 4 W | % Liothyronine | nt | nt | 1.7 | 3.1 | nt |
| | % largest unknown impurity | nt | nt | 0.09 | 0.55 | nt |
| | % total impurities | nt | nt | 2.1 | 4.2 | nt |
| 40° C., 4 W | % Liothyronine | nt | nt | 0.9 | 0.4 | nt |
| | % largest unknown impurity | nt | nt | 0.12 | 0.12 | nt |
| | % total impurities | nt | nt | 1.7 | 0.6 | nt |
| 25° C., 3 M | % Liothyronine | nt | nt | 0.6 | 0.35 | nt |
| | % largest unknown impurity | nt | nt | 0.46 | 0.11 | nt |
| | % total impurities | nt | nt | 1.51 | 0.71 | nt |
| 40° C., 3 M | % Liothyronine | nt | nt | 1.56 | 0.87 | nt |
| | % largest unknown impurity | nt | nt | 0.48 | 0.16 | nt |
| | % total impurities | nt | nt | 2.66 | 1.35 | nt | nt = not tested

The results described in Table 1 demonstrate reduced liothyronine and total impurities were detected in levothyroxine formulations having a pH of 9-10 as compared to pH 8.

The effect of pH on levothyroxine stability was further tested in samples having a pH 9.5-11.5. Separate samples containing levothyroxine sodium at a concentration of 20 mcg/mL or 100 mcg/mL, tromethamine at a concentration of 10 mg/mL in normal saline were adjusted to various pH levels. 5 mL of each sample was filled into 10 cc amber tubing vials, and the vials were stoppered with 20 mm stoppers under nitrogen. The samples were stored at temperatures of 25° C., 40° C., and 55° C. The samples stored at 55° C. were analyzed by HPLC at 1 W and 2 W of storage. The samples stored at 25° C. and 40° C. were analyzed by HPLC at 2M of storage using the HPLC conditions described hereinabove.

The results for liothyronine, largest unknown impurity, and total impurities as determined by peak area percent are set forth in Table 2.

TABLE 2

| | | | | | |
|---|---|---|---|---|---|
| Levothyroxine Na (mcg/mL) | | 20 | 20 | 100 | 20 |
| Tromethamine (mg/mL) | | | 10 | | |
| Solvent | | | Normal saline | | |
| pH | | 9.5 | 10.4 | 10.4 | 11.5 |
| 55° C., 1 W | % Liothyronine | 0.9 | 0.2 | 0.3 | 0.1 |
| | % largest unknown impurity | 0.09 | 0.09 | 0.11 | 0.08 |
| | % total impurities | 1.2 | 0.5 | 0.7 | 0.4 |
| 55° C., 2 W | % Liothyronine | 1.9 | 0.4 | 0.8 | 0.2 |
| | % largest unknown impurity | 0.1 | 0.1 | 0.11 | 0.1 |
| | % total impurities | 2.0 | 0.9 | 1.1 | 0.4 |

TABLE 2-continued

| | | | | | |
|---|---|---|---|---|---|
| Levothyroxine Na (mcg/mL) | | 20 | 20 | 100 | 20 |
| Tromethamine (mg/mL) | | | 10 | | |
| Solvent | | | Normal saline | | |
| pH | | 9.5 | 10.4 | 10.4 | 11.5 |
| 25° C., 2 M | % Liothyronine | 0.34 | 0.17 | 0.23 | 0.34 |
| | % largest unknown impurity | 0.11 | 0.20 | 0.11 | 15.4 |
| | % total impurities | 0.7 | 0.6 | 0.6 | 19.6 |
| 40° C., 2 M | % Liothyronine | 1.00 | 0.38 | 0.49 | 0.31 |
| | % largest unknown impurity | 0.14 | 0.22 | 0.10 | 9.2 |
| | % total impurities | 1.44 | 0.88 | 0.8 | 12.1 |

The results described in Table 2 demonstrate that reduced liothyronine and/or total impurities were detected in levothyroxine formulations having a pH of 10.4 as compared to pH 9.5 or 11.5 following storage at 25° C. or 40° C. for 2M.

Example 2

This example demonstrates the stability of exemplary formulations comprising levothyroxine sodium, sodium iodide, and tromethamine as a function of sodium iodide concentration and pH of the formulation.

Separate samples containing 20 mcg/mL levothyroxine sodium, 10 mg/mL tromethamine, 5.4 mg/mL sodium chloride, and sodium iodide at a concentration of 280 mcg/mL, 140 mcg/mL, or 6 mcg/mL in water were adjusted to various pH levels. 5 mL of each sample was filled into 10 cc flint molded vials, and the vials were stoppered with 20 mm stoppers under nitrogen. The samples were stored at temperatures of 25° C. or 55° C. for 4 W prior to analysis by HPLC.

The HPLC conditions were as follows:

Column: ACE Excel 3 C18-PFP, 4.6×150 mm HPLC column

Mobile Phase A: Sodium heptanesulfonate/Acetonitrile/Water/Methanol/$H_3PO_4$ (4.0 g/800 mL/1600 mL/1600 mL/4.0 mL)

Mobile Phase B: Sodium heptanesulfonate/Acetonitrile/Water/Methanol/$H_3PO_4$ (4.0 g/2000 mL/200 mL/1800 mL/4.0 mL)

Diluent: 0.01 N NaOH

Column temperature: 25° C.

Flow rate: 1.5 mL/min

Injection volume: 80 μL

Autosampler temperature: 5° C.

Detection: UV at 225 nm

Separation mode: Gradient

Gradient program:

| Time (minutes) | % Mobile Phase A | % Mobile Phase B |
| --- | --- | --- |
| 0 | 100 | 0 |
| 25 | 100 | 0 |
| 40 | 10 | 90 |
| 50 | 10 | 90 |
| 51 | 100 | 0 |
| 60 | 100 | 0 |

The relative response time (RRT) for liothyronine to levothyroxine was approximately 0.71.

The results for liothyronine, largest any other individual impurity (AOII), and total impurities as determined by peak area percent are set forth in Table 3.

TABLE 3

| | | | | | | | | |
| --- | --- | --- | --- | --- | --- | --- | --- | --- |
| Levothyroxine Na (mcg/mL) | | | 20 | | | | | |
| Tromethamine (mg/mL) | | | 10 | | | | | |
| Solvent | | | 5.4 mg/mL sodium chloride in water | | | | | |
| NaI (mcg/mL) | | | 280 | | | 140 | | 6 |
| pH | | | 9.5 | 10 | 10.5 | 9.5 | 10 | 10.5 | 10.5 |
| 25° C., 4 W | % Liothyronine | | 0.28 | 0.26 | 0.26 | 0.28 | 0.27 | 0.26 | 0.25 |
| | % AOII | | 0.56 | 0.55 | 0.57 | 0.52 | 0.55 | 0.6 | 0.33 |
| | % total impurities | | 1.58 | 1.61 | 1.66 | 1.51 | 1.64 | 1.75 | 1.9 |
| 55° C., 4 W | % Liothyronine | | 1.63 | 1.06 | 0.71 | 1.74 | 1.06 | 0.74 | 0.87 |
| | % AOII | | 0.53 | 0.54 | 0.53 | 0.59 | 0.61 | 0.53 | 0.99 |
| | % total impurities | | 3.24 | 2.76 | 2.43 | 3.6 | 2.86 | 2.49 | 3.5 |

The samples also were stored at temperatures of 25° C. or 40° C. for 2M or 4M prior to analysis by HPLC.

The HPLC conditions were as follows:

Column: Phenomenex Kinetex 2.6 μm C18, 4.6×150 mm HPLC column

Mobile Phase A: 0.05 M Sulfamic Acid, pH 2.0

Mobile Phase B: Acetonitrile

Diluent: 10% Mobile Phase A in Methanol: Acetonitrile: Mobile Phase A (1000 mL: 300 mL: 700 mL)

Column temperature: 27° C.

Flow rate: 1.2 mL/min

Injection volume: 50 μL

Autosampler temperature: 25° C.

Detection: UV at 225 nm

Separation mode: Gradient

Gradient program:

| Time (minutes) | % Mobile Phase A | % Mobile Phase B |
| --- | --- | --- |
| 0 | 70 | 30 |
| 5 | 70 | 30 |
| 33 | 32 | 68 |
| 35 | 32 | 68 |
| 36 | 70 | 30 |
| 50 | 70 | 30 |

The relative response time (RRT) for liothyronine to levothyroxine was approximately 0.62.

The results for liothyronine, largest any other individual impurity (AOII), and total impurities as determined by peak area percent are set forth in Table 4.

TABLE 4

|  |  | \multicolumn{7}{c}{} |
|---|---|---|---|---|---|---|---|---|
| | Levothyroxine Na (mcg/mL) | \multicolumn{7}{c}{20} |
| | Tromethamine (mg/mL) | \multicolumn{7}{c}{10} |
| | Solvent | \multicolumn{7}{c}{5.4 mg/mL sodium chloride in water} |
| | NaI (mcg/mL) | 280 | | | 140 | | | 6 |
| | pH | 9.5 | 10 | 10.5 | 9.5 | 10 | 10.5 | 10.5 |
| 25° C., 2 M | % Liothyronine | 0.28 | 0.24 | 0.23 | 0.29 | 0.25 | 0.24 | 0.26 |
| | % AOII | 0.11 | 0.12 | 0.11 | 0.09 | 0.10 | 0.12 | 0.46 |
| | % total impurities | 0.81 | 0.8 | 0.85 | 0.76 | 0.77 | 0.88 | 1.85 |
| 40° C., 2 M | % Liothyronine | 0.9 | 0.55 | 0.39 | 0.88 | 0.55 | 0.41 | 0.43 |
| | % AOII | 0.13 | 0.13 | 0.17 | 0.14 | 0.14 | 0.15 | 0.91 |
| | % total impurities | 1.56 | 1.2 | 1.07 | 1.42 | 1.18 | 1.09 | 2.5 |
| 25° C., 4 M | % Liothyronine | 0.35 | 0.28 | 0.25 | 0.35 | 0.28 | 0.26 | 0.25 |
| | % AOII | 2.14 | 0.17 | 0.11 | 0.18 | 0.17 | 0.17 | 1.21 |
| | % total impurities | 3.26 | 0.93 | 1.04 | 1.00 | 0.93 | 0.94 | 2.81 |
| 40° C., 4 M | % Liothyronine | 1.23 | 0.84 | 0.58 | 1.3 | 0.86 | 0.59 | 0.6 |
| | % AOII | 0.52 | 1.38 | 1.07 | 0.72 | 0.92 | 0.69 | 1.45 |
| | % total impurities | 2.76 | 3.23 | 2.72 | 2.84 | 2.73 | 2.14 | 3.51 |

The results described in Tables 3 and 4 demonstrate that levels of liothyronine in formulations comprising 140 mcg/mL or 280 mcg/mL sodium iodide were decreased as the pH was increased from 9.5 to 10 and from 10 to 10.5 following storage at 55° C. for 4 W or at 40° C. for 2M or 4M. The levels of total impurities in formulations comprising 140 mcg/mL sodium iodide also were decreased as the pH was increased from 9.5 to 10 and from 10 to 10.5 following storage at 55° C. for 4 W or at 40° C. for 2M or 4M. Lower levels of AOII and total impurities were detected in formulations comprising 140 mcg/mL or 280 mcg/mL sodium iodide at pH 10.5 as compared to formulations comprising 6 mcg/mL sodium iodide at pH 10.5 following storage at 55° C.° for 4 W or at 40° C. for 2M or 4M.

Example 4

This example demonstrates the stability of exemplary formulations comprising levothyroxine sodium, sodium iodide, and tromethamine as a function of vial type.

An aqueous solution containing 20 mcg/mL levothyroxine sodium, 10 mg/mL tromethamine, 5.4 mg/mL sodium chloride, and 6 mcg/mL sodium iodide was adjusted to pH 10.5. 5 mL of the solution was filled into each of the vials described in Table 5, and the vials were stoppered under nitrogen.

TABLE 5

| | Type | Size | Color | Glass vial preparation | Inner surface treatment |
|---|---|---|---|---|---|
| Vial 1 | Glass | 10 cc | Flint | Molded | No |
| Vial 2 | Glass | 10 cc | Amber | Molded | (NH$_4$)$_2$SO$_4$ |
| Vial 3 | Glass | 5 cc | Amber | Tubing | (NH$_4$)$_2$SO$_4$ |
| Vial 4 | Glass | 6 cc | Flint | Molded | No |
| Vial 5 | Plastic[1] | 10 cc | Opaque | N/A | N/A |
| Vial 6 | Plastic[2] | 10 cc | Opaque | N/A | N/A |
| Vial 7 | Plastic[3] | 10 cc | Clear | N/A | N/A |
| Vial 8 | Plastic[3] | 10 cc | Amber | N/A | N/A |
| Vial 9 | Plastic[4] | 10 cc | Clear | N/A | Silicon |
| Vial 10 | Plastic[4] | 10 cc | Amber | N/A | Silicon |

[1]polypropylene copolymer - ExxonMobil PP9122
[2]polypropylene copolymer - Flint Hills Resources 23M2A
[3]cyclic olefin polymer - Daikyo CRYSTAL ZENITH ™
[4]cyclic olefin polymer - SiO$_2$ Medical Products The vials were stored at a temperature of 25° C. or 55° C. for 4 W prior to analysis by HPLC. The HPLC conditions were the same as described hereinabove for the data of Table 3. The results for liothyronine (T3), largest any other individual impurity (AOII), and total impurities as determined by peak area percent are set forth in Table 6.

TABLE 6

| | \multicolumn{6}{c}{Storage Temp} |
|---|---|---|---|---|---|---|
| | \multicolumn{3}{c}{25° C.} | \multicolumn{3}{c}{55° C.} |
| Impurity | T3 | AOII | Tot | T3 | AOII | Tot |
| Vial 1 | 0.25 | 0.33 | 1.9 | 0.87 | 0.99 | 3.5 |
| Vial 2 | 0.28 | 0.39 | 2 | 1.59 | 4.97 | 14.6 |
| Vial 3 | 0.25 | 2.54 | 4.4 | 0.91 | 2.31 | 4.9 |
| Vial 4 | 0.22 | 0.52 | 2.5 | 1.11 | 4.02 | 7.9 |
| Vial 5 | 0.25 | 0.7 | 3.4 | 0.85 | 8.76 | 20.3 |
| Vial 6 | 0.25 | 0.89 | 3.7 | 0.73 | 10.51 | 29.9 |
| Vial 7 | 0.24 | 0.75 | 2.6 | 0.78 | 7.29 | 10.7 |
| Vial 8 | 0.24 | 0.81 | 2.7 | 0.75 | 7.09 | 10.6 |
| Vial 9 | 0.25 | 0.48 | 1.9 | 0.78 | 2.79 | 5.4 |
| Vial 10 | NT | NT | NT | 0.76 | 3 | 5.7 |

The results described in Table 6 demonstrate that vial material, size, color, and/or treatment can affect the stability of formulations comprising levothyroxine sodium, sodium iodide, and tromethamine.

Example 5

This example demonstrates the stability of comparative formulations comprising levothyroxine sodium, glycerol, sodium chloride, and water as a function of the pH of the formulation.

Separate samples containing levothyroxine sodium at a concentration of 20 mcg/mL and glycerol at a concentration of 100 mg/mL in normal saline were adjusted to pH levels of 7, 8, and 9. 5 mL of each sample was filled into 10 cc amber tubing vials, and the vials were stoppered with 20 mm stoppers under nitrogen. The samples were stored at a temperature of 55° C. The samples were analyzed by HPLC at 1 week of storage using the HPLC conditions described in Example 1. The results for liothyronine, largest unknown impurity, and total impurities as determined by peak area percent are set forth in Table 7.

TABLE 7

|  |  | \multicolumn{3}{c}{} |  |  |
| --- | --- | --- | --- | --- |
|  | Levothyroxine Na (mcg/mL) | \multicolumn{3}{c}{20} |
|  | Glycerol (mg/mL) | \multicolumn{3}{c}{100} |
|  | Solvent | \multicolumn{3}{c}{Normal saline} |
|  | pH | 7 | 8 | 9 |
| 55° C., 1 W | % Liothyronine | 3.6 | 3.4 | 2.4 |
|  | % largest unknown impurity | 1.16 | 1.30 | 0.82 |
|  | % total impurities | 5.3 | 5.4 | 3.8 |

The results described in Table 7 demonstrate that high levels of impurities are formed in levothyroxine formulations containing glycerol over the pH range 7-9 following storage at 55° C. for one week.

Example 6

This example demonstrates a method for preparing an exemplary formulation of the invention.

The composition of an exemplary formulation containing 100 mcg levothyroxine in 5 mL volume is as described in Table 8.

TABLE 8

| Component | Quantity per mL |
| --- | --- |
| Levothyroxine sodium, USP | 20 mcg |
| Sodium chloride | 6.48 mg |
| Sodium iodide | 0.14 mg |
| Tromethamine, USP | 10 mg |
| Sodium hydroxide (1N) | As needed to adjust pH to 10-10.5 |
| Hydrochloric acid (1N) | (target 10.3) |
| Purified water | q.s. |

The compositions for exemplary formulations containing 200 mcg or 500 mcg levothyroxine in 5 mL volume are the same as described in Table 8, except that the concentrations of levothyroxine sodium are 40 mcg/mL and 100 mcg/mL, respectively.

An exemplary formulation is prepared by filling purified water in an amount of approximately 80% of a predetermined final batch volume into a suitable container. The entire amounts of sodium chloride, sodium iodide, and tromethamine are added in succession, with mixing until dissolution of each ingredient prior to addition of the next ingredient. The pH is determined, and then adjusted to pH 10.3 (range of 10.0 to 10.5) with sodium hydroxide and/or hydrochloric acid. The entire amount of levothyroxine sodium is added to the container, and the solution is mixed until dissolution. The pH is determined, and then adjusted to pH 10.3 (range of 10.0 to 10.5) with sodium hydroxide and/or hydrochloric acid. Purified water is added in an amount sufficient to reach the predetermined batch volume with continued mixing to ensure complete dissolution of all ingredients. The formulation can be bubbled with nitrogen or other suitable gas throughout the compounding to limit the dissolved oxygen in the formulation. Under aseptic conditions, the solution is filtered through a 0.22 μm filter, and then 5 mL of the filtered solution is filled into containers (e.g. vials) under nitrogen. The containers are then sealed (e.g., stoppered) under nitrogen.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical product comprising a liquid formulation comprising levothyroxine or a pharmaceutically acceptable salt thereof, a stabilizing agent comprising an amine selected from one or more of tromethamine, bis(2-hydroxyethyl)-imino-tris(hydroxymethyl)methane, monoethanolamine, diethanolamine, triethanolamine, 2-amino-2-methyl-1,3-propanediol, 2-dimethylamino-2-methyl-1-propanediol, 2-amino-2-ethylpropanol, 2-amino-1-butanol, and 2-amino-2-methyl-1-propanol, and water, wherein the formulation retains at least 95% of the initial concentration of levothyroxine or pharmaceutically acceptable salt thereof after storage for two months at 40° C. and retains at least 95% of the initial concentration of levothyroxine or pharmaceutically acceptable salt thereof after storage for at least 12 months at room temperature.

2. The pharmaceutical product of claim 1, wherein the levothyroxine or a pharmaceutically acceptable salt thereof is levothyroxine sodium.

3. The pharmaceutical product of claim 2, wherein levothyroxine sodium is present at a concentration of from about 5 mcg/mL to about 500 mcg/mL.

4. The pharmaceutical product of claim 1, wherein the amine is tromethamine which is present at a concentration of about 1 mg/mL to about 50 mg/mL.

5. The pharmaceutical product of claim 1, wherein the stabilizing agent further comprises a salt of iodine.

6. The pharmaceutical product of claim 5, wherein the salt of iodine is sodium iodide or potassium iodide.

7. The pharmaceutical product of claim 6, wherein the salt of iodine is sodium iodide which is present at a concentration of about 10 mcg/mL to about 500 mcg/mL.

8. The pharmaceutical product of claim 1, wherein the formulation has a pH of from about 9.0 to about 11.5.

9. The pharmaceutical product of claim 8, wherein the formulation has a pH of from about 9.8 to about 10.8.

10. The pharmaceutical product of claim 1, wherein the formulation contains not more than 2.0% liothyronine (T3).

11. The pharmaceutical product of claim 1, wherein the formulation contains not more than 5.0% total impurities.

12. The pharmaceutical product of claim 1, wherein the formulation retains at least about 90% of the initial concentration of levothyroxine or pharmaceutically acceptable salt thereof after storage for at least 18 months at room temperature.

13. The pharmaceutical product of claim 1, wherein the formulation does not contain a buffer.

14. The pharmaceutical product of claim 1, wherein the formulation is contained within a clear glass container.

15. The pharmaceutical product of claim 14, wherein the clear glass container is a flint colored, molded vial, ampoule, cartridge, or syringe.

16. The pharmaceutical product of claim 14, wherein the clear glass container is not treated with ammonium sulfate.

\* \* \* \* \*